United States Patent [19]

Poudrier et al.

[11] Patent Number: 4,990,445
[45] Date of Patent: Feb. 5, 1991

[54] STABLE REAGENT AND KINETIC ASSAY FOR ALPHA-AMYLASE

[75] Inventors: Sandra M. Poudrier; Mark T. Oyen, both of San Diego, Calif.

[73] Assignee: Beckman Instruments, Inc., Fullerton, Calif.

[21] Appl. No.: 146,015

[22] Filed: Jan. 20, 1988

[51] Int. Cl.$^5$ .......................... C12Q 1/40; C12Q 1/00
[52] U.S. Cl. .......................................... 435/22; 435/4; 435/15; 435/26; 435/19; 435/21; 435/810
[58] Field of Search ................ 435/22, 4, 15, 26, 810, 435/11, 19, 20, 28, 21

[56] References Cited

U.S. PATENT DOCUMENTS

| | | | |
|---|---|---|---|
| 3,413,198 | 11/1968 | Deutsch | 435/4 |
| 4,036,697 | 7/1977 | Pierre et al. | 195/99 |
| 4,097,336 | 1/1978 | Pierre et al. | 195/99 |
| 4,102,747 | 7/1978 | Driscoll et al. | 435/22 |
| 4,225,672 | 9/1980 | Hall | 435/22 |
| 4,450,232 | 5/1984 | Sanford et al. | 435/15 |

OTHER PUBLICATIONS

Hirose et al., "The Formation of Glucose 1,6 Diphosphate from . . . ", *Agr. Biol. Chem.* 36(12), 2157–2162 (1972).
Hirose et al., "Multifunctional Properties of Beef Liver Phosphoglucomatase", *Agr. Biol. Chem.* 40(12), 2433–2439 (1976).
Lehninger, *Principles of Biochemistry*, Worth Publishers, New York, N.Y., (1982), p. 408.
Possonneau et al., "Glucose 1,6–Diphosphate Formation by Phosphoglucomutase in Mammalian Tissues", *J. Biol. Chem.*, 244(4), 902–909 (1969).
Belocopitow et al., "A Specific Method for the Quantitative Determination of B–Glucose-1–Phosphate", *Anal. Biochem.*, 53, 108–114 (1973).
Ben-Zvi et al., "A Phosphoglucomutase Specific for B–Glucose 1–Phosphate", *Biol. Chem.*, 236(8), 2186–2189 (1961).

Primary Examiner—Esther L. Kepplinger
Assistant Examiner—Toni Scheiner
Attorney, Agent, or Firm—William H. May; Arnold Grant

[57] ABSTRACT

A stable reagent and kinetic assay for α-amylase is provided. The reagent comprises a substrate for the α-amylase and various enzymes and cofactors necessary to produce NADH as the end-product of a series of four reactions. The substrate, enzymes, and cofactors are provided in sufficient excess that the α-amylase from the test sample is the rate-limiting factor. The concentration of α-amylase in a test sample is determined by measuring the rate of increase in absorbance caused by the production of NADH. The use of the novel cofactor fructose-1,6-diphosphate has been found to impart improved stability to the reagent.

26 Claims, 2 Drawing Sheets

ACTION OF AMYLASE ON STARCH

ACTION OF AMYLASE ON STARCH

REGRESSION ANALYSIS OF AMYLASE RECOVERY

STABLE REAGENT AND KINETIC ASSAY FOR ALPHA-AMYLASE

BACKGROUND OF THE INVENTION

1. Alpha-amylase

Alpha-amylase [α(1→4)-glucan 4-glucanohydrolase-]is an enzyme which participates in the digestion of starch in the human gastrointestinal tract. The enzyme is produced in the pancreas and parotid glands of humans where it is secreted into pancreatic juice and saliva, respectively. The α-amylase enzyme can also be found in low but measurable quantities in body fluids such as blood serum and urine.

The concentration of α-amylase in a patient's test sample, such as a serum or urine sample, may exhibit changes which are of clinical significance. Changes in test sample α-amylase concentration can be observed due to a variety of pathological conditions. For example, the test sample taken from a patient afflicted with pancreatitis, mumps or pancreatic cancer will generally show a much higher level of α-amylase than a test sample from a healthy donor. Liver diseases, on the other hand, will generally cause lower α-amylase levels than would be observed in a healthy individual.

Starches form the basic molecular storage reservoirs for plants. As such, they also provide a common energy source in the human diet. The α-amylase produced in humans participates in the digestion of this starch. All starches are homogenous, containing only D-glucose residues. Rather than single molecules, these starches are normally mixtures of two structurally distinct polysaccharides. One component is termed amylose, the other amylopectin. Both are poly-α-D-glucose molecules. Amylose is a linear molecule with all glucose residues linked via α(1→4) bonds. Amylopectin, on the other hand, is a branched molecule due to the presence of a small number of α(1→6) linkages at various points along a core chain consisting of α(1→4) linkages.

Both α-amylase and α-amylase (produced in plants) attack the amylose and amylopectin fractions of starch at α(1→4) sites but in a different pattern. Cleavage with α-amylase is random, occurring at different loci to yield a mixture of glucose and maltose; maltose being a disaccharide consisting of two D-glucose residues connected through an α(1→4) linkage. The action of β-amylase is more ordered, characterized by successive removal of only maltose units, beginning at a non-reducing terminus. See FIG. 1. Neither enzyme is capable of hydrolyzing the α(1→6) linkages. Thus, whereas the combined action of the two enzymes will completely degrade amylose to glucose and maltose, amylopectin is only partially degraded However, other catalysts, called debranching enzymes, specific for hydrolyzing the α(1→6) linkage, do exist in nature.

2. Techniques for Measuring Alpha-amylase

Techniques for determining α-amylase concentrations generally involve the use of starch because of the catalytic effect of α-amylase on the hydrolysis of the α(1→4) linkages of the amylose and amylopectin fractions of starch. If this hydrolysis is left to go to completion, the α-amylase will progressively degrade the starch into glucose, maltose, and oligosaccharides. Certain techniques have attempted to correlate the α-amylase concentration of a test sample with the decrease in the turbidity or viscosity observed in an aqueous starch solution after hydrolysis of the starch with the α-amylase from the test sample. Where a dyed starch is employed as the substrate, the rate of dye released from the dyed starch through α-amylase hydrolysis can also be used as a measure of α-amylase concentration.

A similar technique for measuring α-amylase concentration is the iodometric method which utilizes the well known reaction between iodine and starch to form a blue color. When a blue colored starch-iodine solution is hyrolyzed with α-amylase, the blue color decreases as the α-amylase degrades the starch. The change in color of the blue starch-iodine solution is thus some measure of α-amylase concentration This technique, however, has not been considered reliable or sufficiently definite because it is believed that the change in color does not bear a linear relationship to the concentration of α-amylase.

Other more sophisticated techniques utilize the quantity of reducing substances, such as glucose or maltose, produced by the α-amylase hydrolysis of starch, as a measure of the α-amylase concentration in a test sample. For example, enzymatic techniques have been developed which measure α-amylase concentration by using α-amylase and other enzymes to hydrolyze starch into α-amylase. The glucose is then measured, in turn, through coupled enzymatic reactions. This approach, however, is not entirely satisfactory because of the natural presence of glucose in many test samples The glucose contributed by these test samples will react through the same coupled enzymatic reactions to produce easily detectable product in addition to the product ultimately generated by the glucose which is released through α-amylase hydrolysis of the starch. The concentration of the endogenous glucose in a test sample is generally of sufficient concentration, with respect to the amount of glucose typically liberated through α-amylase hydrolysis, that erroneous results are obtained where the endogenous glucose from a test sample is allowed to contribute to the observed signal in a given assay. As a result, such pre-existing glucose must be eliminated from the test sample before the assay is conducted.

U.S. Pat. No. 4,036,697, which is incorporated herein by reference, discloses a kinetic assay for detecting α-amylase in a test sample which overcomes many of the problems encountered with the previously mentioned prior art methods In particular, this kinetic assay eliminates interference from endogenous glucose without requiring a separate removal step. The kinetic assay measures the rate of NADH produced as the result of a series of four coupled reactions:

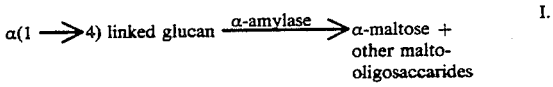
I.

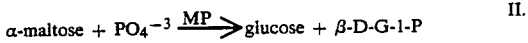
II.

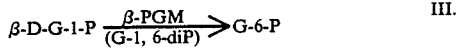
III.

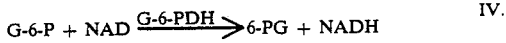
IV.

wherein:

| | |
|---|---|
| PO$_4^{-3}$ | = phosphate ion |
| MP | = maltose phosphorylase |
| β-D-G-1-P | = β-D-glucose-1-phosphate |

-continued

| G-1,6-diP | = glucose-1,6-diphosphate |
| β-PGM | = β-D-phosphoglucomutase |
| G-6-P | = glucose-6-phosphate |
| G-6-PDH | = glucose-6-phosphate dehydrogenase |
| 6-PG | = 6-phosphogluconate |
| NAD | = β-nicotinamide-adenine dinucleotide |
| NADH | = reduced form of NAD |

The α-amylase from a test sample directly participates in the first reaction of this series. The α(1→4) linked glucan, phosphate ions, MP, β-PGM, and G-6-PDH are provided in sufficient excess such that the α-amylase from a test sample is the rate limiting factor in the sequence of reactions. In other words, the observed reaction rate for the complete series of reactions is determined by the rate of the first α-amylase catalyzed reaction, which is, in turn, determined by the amount of α-amylase in a test sample.

The third reaction in this series generally requires a cofactor for the β-PGM. The use of a cofactor for β-PGM, such as glucose-1,6-diphosphate (G-1,6-diP), accelerates the third reaction in this four-reaction series. The β-PGM ordinarily requires the β-form of G-1,6-diP for activity It is believed by some that the α-form of the G-1,6-diP may also work effectively as a cofactor in the β-PGM catalyzed reaction, although most naturally occurring enzymes are very specific for their corresponding substrates and intermediates.

The β-G-1,6-dip is not readily available commercially, and its production must be incorporated into the manufacturing process for the amylase reagent Nonetheless, β-G-1,6-diP is the recognized and accepted cofactor for β-PGM. It is believed that β-G-1,6-diP operates as a cofactor by functioning as the β-G-1,6-diP intermediate in the β-PGM catalyzed reaction which converts β-D-G-1-P to G-6-P. In the absence of such a cofactor, there is a delay in completion of the β-PGM catalyzed reaction due to the time required to build up a sufficient amount of the G-1,6-diP intermediate to push the reaction forward The kinetic assay and reagent of U.S. Pat. No. 4,036,697 overcomes the prior art problems of glucose interference by removing the participation of glucose in the chain of reactions leading to the measurable NADH production. Specifically, the glucose produced in the second reaction does not participate in further reactions in this series. Instead, the β-D-G-1-P product of the second reaction participates in the third and fourth reactions.

It is generally preferred that the kinetic α-amylase assay reagents of U.S. Pat. No. 4,036,697 be provided as one mixture, or combined reagent, to facilitate handling and use, although a dry mixture can be provided which is subsequently reconstituted with deionized water or a similar aqueous medium such as a buffer. The reconstituted reagent has exhibited moderate storage stability, but it would be desirable to have a kinetic α-amylase assay reagent which exhibits greater stability in its reconstituted form. It would also be advantageous to have a cofactor for β-PGM that is readily available commercially.

3. Fructose-1,6-diphosphate

It has been reported that α-D-G-1,6-diP can be synthesized by α-PGM from α-D-G-1-P and fructose-1,6-diP (F-1,6-diP) Possonneau, Janet V., Oliver H. Towry, Demoy W. Schulz, and Joseph G. Brown, Glucose 1,6-Diphosphate Formation by Phosphoglucomutase in Mammalian Tissues, J. Biol. Chem., 244 (4), 902-909 (1969). As previously indicated, it is believed by some that α-D-G-1,6-diP can function as a cofactor in the β-PGM catalyzed reaction of β-D-G-1-P to G-6-P, although this has not been demonstrated. In any event, the rate of synthesis of α-D-G-1,6-diP from α-D-G-1-P and F-1,6-diP has been reported to be relatively slow. Id.

A commercially available product such as F-1,6-diP would be advantageous for incorporation into the rate method of U.S. Pat. No. 4,036,697, provided that the F-1,6-diP and β-D-G-1-P could similarly be catalyzed by β-PGM to produce the required G-1,6 diP cofactor. However, the reported length of time required for the F-1,6-diP to produce the G-1,6-diP cofactor negates the advantage of commercial availability of the F-1,6-diP product It would be desirable to have a commercially available product that could act directly as a cofactor for B-βPGM or that could produce the recognized G-1,6-diP more rapidly than has been reported for the F-1,6-diP starting material.

SUMMARY OF THE INVENTION

A reagent and kinetic assay for α-amylase are provided in accordance with the present invention. The reagent of the present invention utilizes commercially available F-1,6-diP directly as the cofactor for the β-PGM catalyzed conversion of G-1-P to G-6-P, and has surprisingly been found to exhibit much greater reconstituted stability than prior art reagents for use in kinetic α-amylase assays.

The kinetic assay for α-amylase using the stable reagent of the present invention employs the following series of reactions:

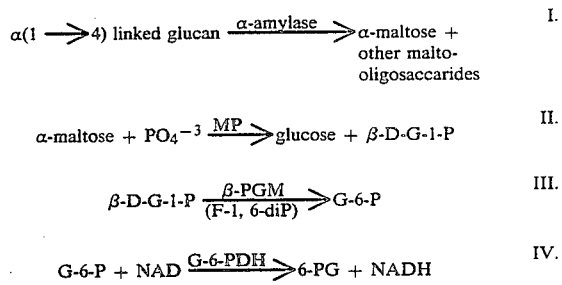

wherein:

| $PO_4^{-3}$ | = phosphate ion |
| MP | = maltose phosphorylase |
| β-D-G-1-P | = β-D-glucose-1-phosphate |
| F-1,6-diP | = fructose-1,6-diphosphate |
| β-PGM | = β-D-phosphoglucomutase |
| G-6-P | = glucose-6-phosphate |
| G-6-PDH | = glucose-6-phosphate dehydrogenase |
| 6-PG | = 6-phosphogluconate |
| NAD | = β-nicotinamide-adenine dinucleotide |
| NADH | = reduced form of NAD |

DETAILED DESCRIPTION OF THE INVENTION

Figure 1:
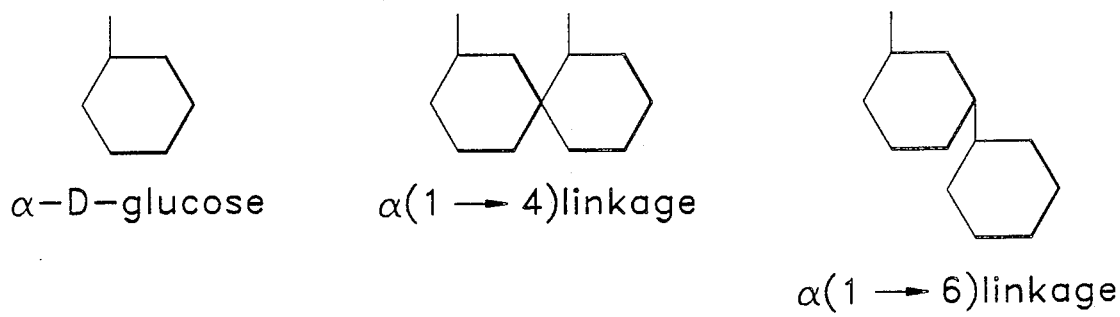
FIG. 1 demonstrates the action of α-amylase and β-amylase on starch.
Figure 1:
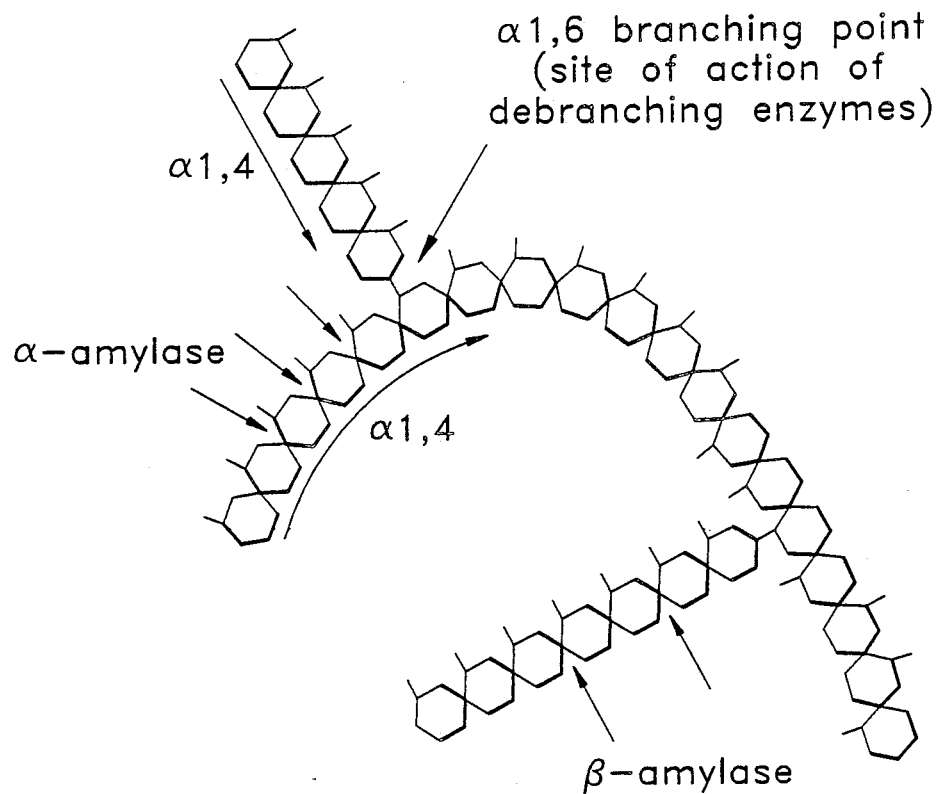

The stable reagent of the present invention contains α(1→4) linked glucan, phosphate ions, MP, β-PGM, F-1,6-diP, β-AND, and G-6-PDH. These constituents may be provided as a single reagent or as a kit wherein a plurality of reagents are employed that upon combination yield the reagent of the present invention.

The reagent of the present invention is intended to be used in a kinetic assay. In such an assay, the rate of formation of the NADH which is ultimately produced must be characteristic of and related to the amount of α-amylase present in a test sample. Thus, all of the constituents of the reagent must be present in sufficient quantity to render the α-amylase contributed by a test sample the rate limiting factor in the series of reactions.

For the assay of aqueous solutions of human serum or urine, it is preferred to use a concentration of between about 1.0 to about 20 grams of a α(1→4) linked glucan per liter of reagent. A glucan concentration of about 5 grams per liter of reagent is used in the preferred embodiment. Similarly, the concentration of phosphate ions should also be at a level to ensure that α-amylase is the rate-limiting compound. However, it is desirable not to have too high of a concentration of phosphate ions because large concentrations may inhibit the activity of the β-PGM enzyme.

It is preferred to have about 0.01 to about 0.1 molar concentration of inorganic phosphate, with about 0.04 molar being the most preferred amount for the assay of serum. At least about 200 international units (IU) of MP per liter of reagent are also required, but about 6000 IU per liter is preferred. β-PGM is present in a concentration of at least about 100 IU per liter of reagent so that the α-amylase contributed by the test sample remains the rate-limiting constituent. It is preferred that 1000 to about 2000 IU of β-PGM per liter of reagent be used when assaying α-amylase in human serum. The preferred concentration of F-1,6-diP should be at least about 0.01 millimoles per liter of reagent, although the optimum concentration is about 0.667 millimoles per liter.

The amount of AND should also be sufficiently high to maintain the α-amylase from a test sample as the rate-limiting constituent A suitable range for the NAD concentration is about 1 to about 10 millimoles per liter of reagent. The preferred concentration of AND is about 2.5 millimoles per liter. β-nicotinamide-adenine dinucleotide phosphate (NADP) may be substituted for NAD in the present invention. The glucose-6-phosphate dehydrogenase (G-6-PDH) should also be present in concentration of at least about 500 IU per liter of reagent so that this reaction is not the rate-limiting reaction. The preferred concentration of the G-6-PDH enzyme is about 6000 IU per liter of reagent.

The α(1→4) linked glucan may be any polysaccharide made up primarily of glucose wherein the glucose molecules are mainly connected through α(1→4) linkages which can be attacked by the α-amylase. Exemplary of such polysaccharides are starch, amylopectin, amylose, glycogen, dextrin and their degraded products, and homologs of maltooligosaccharides such as maltotriose, maltotetraose and maltopentaose or mixtures thereof.

Maltotetraose is the preferred α(1→4) linked glucan for use in the present invention. Maltotetraose is an oligosaccharide consisting of four α(1→4) linked glucose units and is commercially available from Sigma Chemical Company, St. Louis, Missouri, or Boehringer Mannheim, GmbH, Mannheim, West Germany. Where maltotetraose is employed as the α(1→4) linked glucan, the kinetic assay proceeds as follows: Maltotetraose substrate is hydrolyzed by α-amylase in the test sample to yield two moles of maltose per mole of substrate. The enzyme maltose phosphorylase (MP) catalyzes the phosphorolysis of each mole of maltose to one mole each of glucose and β-D-glucose-1-phosphate. The enzyme β-phosphoglucomutase (β-PGM) converts the β-glucose-1-phosphate to glucose-6-phosphate which is then oxidized to 6-phosphogluconate with the concomitant reduction of nicotinamide adenine dinucleotide (NAD) to NADH in the reaction catalyzed by G-6-PDH.

Although maltotetraose contains α(1→4) linked glucose units, the initial hydrolysis of this substrate yields one each of the α-maltose and β-maltose forms. It is therefore preferred to use an excess quantity of maltose mutarotase (MMR) to convert all of the liberated maltose into the α-form. At least about 250 IU of MMR per liter of reagent is required, although an optimum of about 500 IU per liter is preferred.

The rate of NADH production and the conversion of such rate into the concentration of α-amylase is accomplished by known methods One such method uses spectrophotometric means to measure the change in absorbance of light due to the production of NADH at wave lengths ranging from about 300 to about 370 millimicrons (nm) at a temperature range of from about 15° to about 50° C. A wave length of about 340 nm at about 37° C. is preferred.

When the rate of change in absorbance is measured, the concentration of α-amylase may be calculated by the following equation wherein the change in absorbance is measured at a wave length of 340 nm and a temperature of 37° C.:

$$IU/\text{liter} = \frac{\Delta A \times V_t \times 1000}{V_s \times 6.22}$$

ΔA = change of absorbance/minute
V = total reaction volume
$V_s$ = volume of sample containing α-amylase
6.22 = millimolar absorptivity index of NADH at 340 nm The phosphate ions are supplied from any source compatible with the reagent system of the present invention. Inorganic phosphates are an example of such a source. The phosphate used in the preferred embodiment is a mixture of $K_2HPO_4$ and $KH_2PO_4$ which forms a buffered solution at a pH of about 6.5 which is optimum.

The preferred source of maltose phosphorylase is a strain of the microorganism *Lactobacillus brevis* (ATCC8287) which has been cultured by Beckman Instruments, Inc., Microbics Operations of Carlsbad, California and from which the enzyme has been extracted and purified by conventional methods. Other sources of this enzyme are strains of *Neisseria meningitides*, *Neiseri perflava* and other Lactobacilli strains.

The preferred source of β-PGM is *Lactobacillus brevis* (ATCC8287). It is cultured and purified by conventional methods of enzyme purification. Other sources include strains of *Neisseri meningitides*, *Neisseria perflava* and *Euglena gracilis*.

The F-1,6-diP is supplied from any available commercial source. One such commercial source is Boehringer Mannheim GmbH, Mannheim, West Germany.

The preferred source of G-6-PDH is *Leuconostoc mesenteroides* (ATCC 12291) but it may be obtained from other sources.

It is also preferred that divalent cations selected from the class consisting of $Mn^{+2}$, $Mg^{+2}$, $Co^{+2}$, $Zn^{+2}$ or $Ni^{+2}$ be present in the enzyme system to act as a cofactor for $\beta$-PGM. The cations $Mn^{+2}$, $Mg^{+2}$, or $Co^{+2}$ are preferred over $Zn^{+2}$ or $Ni^{+2}$ The cation concentration should be at least about 1 millimole per liter of reagent and is preferably 8.4 millimoles per liter.

Chloride salts such as potassium chloride or sodium chloride may be added to the reagent system to increase the activity of the $\alpha$-amylase Other optional ingredients include mannitol, which may be added as a bulking agent where the reagent is stored in a solid form and subsequently reconstituted into an aqueous reagent, and lactate dehydrogenase (LDH) and NADH which may be added to eliminate interference from pyruvate in some test samples. All of these components are available from a variety of commercial sources Only a small amount of NADH is added to eliminate the interfering pyruvate. This is necessary because pyruvate will react with LDH, which appears as a contaminant in enzyme preparations incorporated into the reagent, consuming some of the NADH ultimately used as a measure of $\alpha$-amylase activity. An excess of LDH is added to drive the pyruvate reaction forward at a rapid rate. This immediately rids the reaction mixture of pyruvate interference so that the measured rate of NADH production is indicative only of $\alpha$-amylase production and not affected by the presence of pyruvate.

Buffers including potassium phosphate dibasic ($K_2HPO_4$) and monobasic ($KH_2PO_4$) can be used to obtain the optimum pH in which to carry out the reaction sequence. Non-phosphate buffers may be used, but are not preferred because phosphate buffers provide a source of phosphate ions. Other buffers include PIPES (piperazine-N,N'-bis[2-ethanesulfonic acid]); TRIS (tris-[hydroxymethyl]aminomethane); HEPES (N-2-hydroxyethylpiperazine-N'-2-ethane sulfonic acid); and triethanolamine. Exemplary of other buffers which may also be satisfactory are ADA (N[2-acetamido]iminodiacetic acid); ACES (N-[2-acetamido]- 2-aminoethanesulfonic acid); and BES (N,N-bis-[2-hydroxyethyl]-2-aminoethanesulfonic acid).

The $\alpha$-amylase reagent of the present invention exhibits a surprisingly marked improvement over the prior art reagent used in kinetic $\alpha$-amylase assays. The reagent of the present invention demonstrated a reconstituted stability of at least 3 days at 25° C. and at least 15 days at 4° C. This compares with stabilities of about 24 hours at 25° C. and about 48 hours at 4° C. for the prior art reagent.

EXAMPLE 1

Formulation

The preferred $\alpha$-amylase reagent of the present invention is compounded in two parts as follows:

TABLE 1

| Solid Form | | |
|---|---|---|
| Description | Concentration | Quantity Per Liter |
| Mannitol | 54.9 mM | 10.0 g |
| Potassium phosphate, monobasic ($KH_2PO_4$) | 12.6 mM | 1.72 g |
| Potassium phosphate, dibasic ($K_2HPO_4$) | 12.4 mM | 2.16 g |
| Potassium chloride (KCL) | 40.0 mM | 2.98 g |
| Nicotinamide adenine dinucleotide trihydrate (NAD) | 2.5 mM | 1.79 g |
| Magnesium Acetate, spray dried | 4.0 mM | 0.57 g |
| Maltotetraose (M4) | 5.0 g/L | 5.0 g |
| Nicotinamide adenine dinucleotide reduced, disodium dried (NADH) | 0.025 mM | 0.0114 g |
| Fructose 1,6-diphosphate (F-1,6-diP) | .667 mM | 0.367 g |
| Maltose phosphorylase, lyophilized | | 6,000 IU |
| Phosphoglucomatose lyophilized | | 1,000 IU |
| Maltosemutarotase, lyophilized (MMR) | | 500 IU |
| Glucose-6-phosphate dehydrogenase, lyophilized (G-6-PDH) | | 6,000 IU |
| Lactate dehydrogenase, lyophilized (LDH) | | 500 IU |

TABLE 2

| Reconstituting Buffer | | |
|---|---|---|
| Description | Concentration | Quantity Per Liter |
| Potassium phosphate, monobasic ($KH_2PO_4$) | 6.85 mM | 0.932 g |
| Potassium phosphate, dibasic ($K_2HPO_4$) | 3.15 mM | 0.549 g |
| Sodium Azide | .05% | 0.5 g |
| Deionized water | — | to volume |

The pH of the reconstituting buffer is adjusted to about 6.0 to about 7.5 with hydrochloric acid (HCl) or sodium hydroxide (NaOH), with a pH of 6.5 being preferred. The solid form is subsequently dissolved in the reconstituting buffer to yield the following mixture:

TABLE 3

| Reconstituted Reagent | | |
|---|---|---|
| Description | Concentration | Quantity Per Liter |
| Mannitol | 54.9 mM | 10.00 g |
| Potassium phosphate, monobasic ($KH_2PO_4$) | 19.45 mM | 2.652 g |
| Potassium phosphate, dibasic ($K_2HPO_4$) | 15.55 mM | 2.709 g |
| Potassium chloride (KCL) | 40.0 mM | 2.98 g |
| Nicotinamide adenine dinucleotide, trihydrate (NAD) | 2.5 mM | 1.790 g |
| Magnesium Acetate, spray dried | 4.0 mM | 0.570 g |
| Sodium azide | .05% | 0.5 g |
| Maltotetraose (M4) | 5.0 g/L | 5.0 g |
| Nicotinamide adenine dinucleotide reduced, disodium dried (NADH) | 0.025 mM | 0.0114 g |
| Fructose 1,6-diphosphate (F-1,6-diP) | .667 mM | 0.367 g |
| Maltose phosphorylase, lyophilized | | 6,000 IU |
| Phosphoglucomatose, lyophilized | | 1,000 IU |
| Maltosemutarotase, lyophilized (MMR) | | 500 IU |
| Glucose-6-phosphate | | 6,000 IU |

TABLE 3-continued

| Description | Reconstituted Reagent Concentration | Quantity Per Liter |
|---|---|---|
| dehydrogenase, lyophilized (G-6-PDH) | | |
| Lactate dehydrogenase, lyophilized (LDH) | | 500 IU |

The preferred reagent may also be made up directly in its final reconstituted form with the pH adjusted as described for the reconstituting buffer. The reagent may be stored and used in this aqueous form, although greater stability and shelf life is achieved where the solid form is stored separately from the buffer and reconstituted as the final aqueous reagent at a later date. Alternately, the dry ingredients for the buffer can be combined with the solid reagent ingredients, and the solid reagent subsequently reconstituted with deionized water.

EXAMPLE 2

Performance

A 4% bovine serum albumin (BSA) solution, pH 7.6, available from Beckman Instruments, Inc., Fullerton, California, was spiked with α-amylase from porcine pancrease in 3.2M $(NH_4)_2SO_4$, pH 6.1, obtained from Sigma Chemical Company, St. Louis, Missouri. The resulting stock solution was determined to contain approximately 2,000 units of activity per liter of α-amylase.

The following dilutions were made from the stock solution, and a kinetic assay run by adding 0.01 mL of each diluted sample to 0.2 mL of the reconstituted reagent of Example 1, and measuring the resulting spectrophotometric change in absorbance at 340 nm:

TABLE 4

| Dilution | Expected Theoretical Value | Observed Value |
|---|---|---|
| 1:14.9 | 134 U/L | 139 U/L |
| 1:7.5 | 267 U/L | 275 U/L |
| 1:5.0 | 400 U/L | 420 U/L |
| 1:3.7 | 540 U/L | 581 U/L |
| 1:3.0 | 667 U/L | 704 U/L |
| 1:2.5 | 800 U/L | 842 U/L |
| 1:2.14 | 934 U/L | 977 U/L |
| 1:1.88 | 1063 U/L | 1099 U/L |
| 1:1.67 | 1198 U/L | 1228 U/L |
| 1:1.5 | 1333 U/L | 1342 U/L |
| 1:1.36 | 1470 U/L | 1461 U/L |
| 1:1.25 | 1600 U/L | 1621 U/L |
| 1:1.15 | 1739 U/L | 1746 U/L |
| 1:1.07 | 1869 U/L | 1860 U/L |
| No Dilution | 2000 U/L | 1973 U/L |

Figure 2:
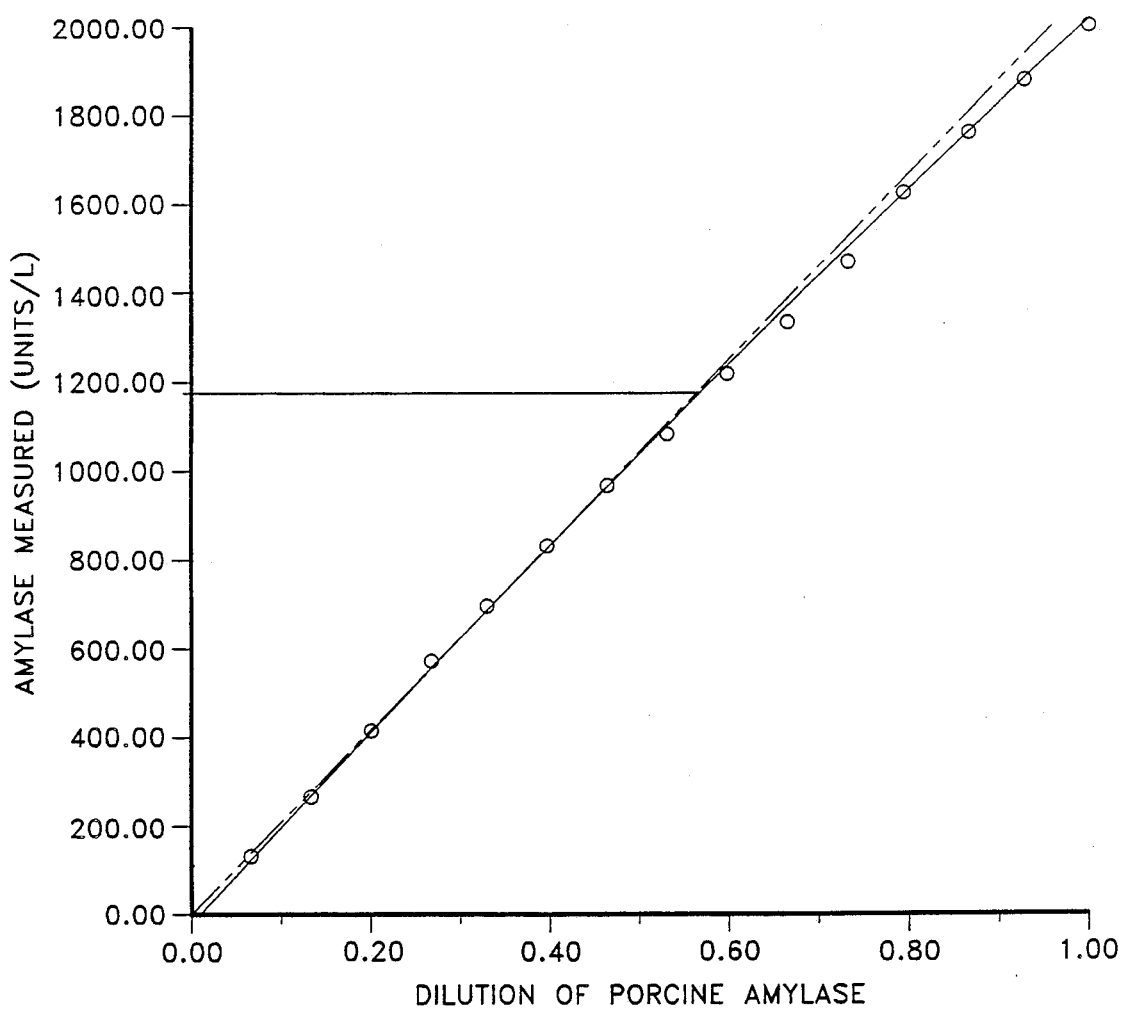
FIG. 2 is a linear regression plot of the performance data from the α-amylase assay of Example 2.

The linearity regression line for these results is shown in FIG. 2. The reconstituted reagent of Example 1 displays linearity to approximately 1200 units per liter of α-amylase in a test sample.

Formulations of the α-amylase reagent of the present invention other than the preferred formulation of Example 1 are contemplated as being within the scope of the invention and will be apparent to those skilled in the art.

As this invention may be embodied in several forms without departing from the essential spirit thereof, the invention is intended to be defined by the appended claims as opposed to the foregoing description.

What is claimed is:

1. A reagent for assaying the amount of α-amylase in a test sample comprising:
   a. a polysaccharide having glucose molecules connected primarily through $\alpha(1\rightarrow 4)$ linkages;
   b. a source of phosphate ions;
   c. maltose phosphorylase;
   d. a coenzyme selected from the group consisting of β-nicotinamide-adenine dinucleotide, B-nicotinamide-adenine-dinucleotide phosphate, and mixtures thereof;
   e. glucose-6-phosphate dehydrogenase;
   f. β-D-phosphoglucomutase; and
   g. fructose-1,6-diphosphate.

2. The reagent of claim 1 wherein said polysaccharide, source of phosphate ions, maltose phosphorylase, coenzyme, glucose-6-phosphate dehydrogenase, β-D-phosphoglucomutase, and fructose-1,6-diphosphate are present in sufficient amounts such that the α-amylase contributed by said test sample is rate-limiting.

3. The reagent of claim 2 wherein said polysaccharide, maltose phosphorylase, coenzyme, glucose-6-phosphate dehydrogenase, β-D-phosphoglucomutase, fructose-1,6-diphosphate, and at least a portion of said source of phosphate ions are in a solid form.

4. The reagent of claim 2 further comprising a cation selected from the group consisting of $Mn^{+2}$, $Mg^{+2}$, $Co^{+2}$, $Zn^{+2}$, $Ni^{+2}$, and mixtures thereof.

5. The reagent of claim 3 further comprising a cation selected from the group consisting of $Mn^{+2}$, $Mg^{+2}$, $Co^{+2}$, $Zn^{+2}$, $Ni^{+2}$, and mixtures thereof.

6. The reagent of claim 4 wherein said cation is $Mg^{+2}$.

7. The reagent of claim 5 wherein said cation is $Mg^{+2}$.

8. The reagent of claim 2 further comprising lactate dehydrogenase and NADH.

9. The reagent of claim 3 further comprising lactate dehydrogenase and NADH.

10. The reagent of claim 2 further comprising maltose mutarotase.

11. The reagent of claim 3 further comprising maltose mutarotase.

12. The reagent of claim 3 wherein said solid form further contains a bulking agent.

13. The reagent of claim 12 wherein said bulking agent is mannitol.

14. The reagent of claim 2 wherein said polysaccharide is an $\alpha(1\rightarrow 4)$ linked glucan.

15. The reagent of claim 3 wherein said polysaccharide is an $\alpha(1\rightarrow 4)$ linked glucan.

16. The reagent of claim 14 wherein said $\alpha(1\rightarrow 4)$ linked glucan is maltotetraose.

17. The reagent of claim 15 wherein said $\alpha(1\rightarrow 4)$ linked glucan is maltotetraose.

18. A reagent for assaying the amount of α-amylase in a test sample comprising per liter of reagent:
   a. at least about 1 gram of a polysaccharide having glucose molecules connected primarily through $\alpha(1\rightarrow 4)$ linkages;
   b. from about 0.01 to about 0.1 moles of phosphate ions;
   c. at least about 200 International Units of maltose phosphorylase;
   d. at least about 1 millimole of a coenzyme selected from the group consisting of β-nicotinamideadenine dinucleotide, β-nicotinamide-adenine dinucleotide phosphate, and mixtures thereof;

e. at least about 500 International Units of glucose-6-phosphate dehydrogenase;

f. at least about 100 International Units of β-D-phosphoglucomutase; and, g. at least about 0.1 millimoles of fructose-1,6-diphosphate.

19. The reagent of claim 18 wherein said polysaccaride, maltose phosphorylase, coenzyme, glucose-6-phosphate dehydrogenase, β-D-phosphoglucomutase, fructose-1,6-diphosphate, and at least a portion of said source of phosphate ions are in a solid form.

20. The reagent of claim 19 wherein said solid form comprises per liter of reconstituted reagent about 0.02 to about 0.03 moles concentration of phosphate ions, and a reconstituting buffer which comprises per liter of reconstituted reagent about 0.01 molar concentration of phosphate ions.

21. The reagent of claim 18 wherein said polysaccaride is an $\alpha(1\rightarrow 4)$ linked glucan.

22. The reagent of claim 21 wherein said $\alpha(1\rightarrow 4)$ linked glucan is maltotetraose.

23. The reagent of claim 21 further comprising the cation $Mg^{+2}$ and maltose mutarotase.

24. The reagent of claim 23 further comprising mannitol.

25. A method for measuring α-amylase in a test sample comprising:
   a. contacting a test sample with the reagent of claim 1; and,
   b. measuring the rate of production of the reduced form of the coenzyme selected from the group consisting of β-nicotinamide-adenine dinucleotide, β-nicotinamide-adenine dinucleotide phosphate, and mixtures thereof.

26. The method of claim 25 wherein said measuring is done spectrophotometrically.

* * * * *